United States Patent [19]

Berghoff et al.

[11] Patent Number: 5,443,065
[45] Date of Patent: Aug. 22, 1995

[54] CONNECTOR FOR MEDICAL DEVICE

[75] Inventors: Gene Berghoff, Eden Prairie; Scott Latterell, Minneapolis; both of Minn.; Paul Monroe, Janesville, Wis.

[73] Assignee: Angeion Corporation, Plymouth, Minn.

[21] Appl. No.: 175,498

[22] Filed: Dec. 30, 1993

Related U.S. Application Data

[63] Continuation of Ser. No. 836,953, Feb. 19, 1992, abandoned, which is a continuation-in-part of Ser. No. 764,626, Sep. 24, 1991, Pat. No. 5,304,209.

[51] Int. Cl.⁶ .............................................. A61B 5/04
[52] U.S. Cl. ..................................... 128/639; 439/380
[58] Field of Search ............... 128/639; 439/380, 391, 439/412, 425, 685

[56] References Cited

U.S. PATENT DOCUMENTS

| | | | |
|---|---|---|---|
| 3,874,762 | 4/1975 | Shott et al. | 439/425 |
| 4,180,078 | 12/1979 | Anderson | 128/419 P |
| 4,262,673 | 4/1981 | Kinney et al. | 128/419 P |
| 4,347,849 | 9/1982 | Congdon | 128/419 P |
| 4,498,478 | 2/1985 | Bourgeois | 128/419 PG |
| 4,891,017 | 1/1990 | Kuhn et al. | 439/380 |
| 4,911,655 | 3/1990 | Pinyan et al. | 439/412 |
| 5,026,301 | 6/1991 | Balyasny et al. | 439/391 |
| 5,145,417 | 9/1992 | Honkomp et al. | 439/685 |

*Primary Examiner*—George Manuel
*Attorney, Agent, or Firm*—Patterson & Keough

[57] ABSTRACT

A temporary pacemaker combines technologies of the implantable pacemaker, the waterproof watch, with a separate remote-control programming unit that communicates with the pacemaker via IR radiation. An LCD readout on the temporary pacemaker continuously reports on current settings, and is monitored periodically, as well as during the setting process. The programming unit is aimed at an IR sensor on the pacemaker, and its dedicated controls are used for setting, with the aid of prompting messages on its own LCD panel. Battery life is about 6–9 months, while that for the lithium battery in the sealed and sterilizable pacemaker approaches five years.

A multi-conductor connector and an adapter for use with a temporary external pacemaker, is disclosed which reduces the complexity of connecting temporary pacing leads, adapters, extension cables, heart wires or other miscellaneous cables to a pacing device. It also reduces the possibility of inadvertent removal/disconnection of these patient connected cable systems, and yet allows for a quick release.

8 Claims, 6 Drawing Sheets

CONNECTOR FOR MEDICAL DEVICE

CROSS REFERENCES TO CO-PENDING APPLICATIONS

This application is a continuation of U.S. Ser. No. 07/836,953, filed Feb. 19, 1992, now abandoned which is a Continuation-in-Part of U.S. Ser. No. 07/764,626, filed Sep. 24, 1991, now U.S. Pat. No.5,304,209, entitled "Remote-Control Temporary Pacemaker" to the same assignee as this patent application.

BACKGROUND OF THE INVENTION

1. Field of the Invention

The present invention relates to temporary pacemakers, also known as wearable external pacemakers, and more particularly pertains to an external pacemaker that is strapped to a patient's arm, chest or another portion of the body, using VELCRO or some other means.

2. Description of the Prior Art

There are several varieties of prior art pacemakers that are placed outside the body to be used temporarily while a patient is awaiting implantation of a permanent pacemaker or during post-operative use and emergency room situations. To use a prior art pacemaker, it is customary to connect a heart wire (hereinafter frequently designated as a lead) through the open chest and connect it to the heart or inserting a disposable lead transcutaneously, inserting it through a vein and into the heart. The external end of the lead or heart wire is, of course, attached to the pacemaker unit, so it follows that the unit must be positioned close to the patient. This is the first primary requirement of a temporary pacemaker.

External pacemakers of the prior art intended for temporary use by new patients have been too bulky to be worn conveniently on the patient's body. In many instances, an extension cable is used between the lead or heart wire and the external pacemaker so that the pacemaker can be placed on an IV pole. As a result, the patient has been uncomfortably constrained by being connected by lead, heart wire, or cable to a comparatively immobile instrument. Added is the mental distress of knowing that even normal motion may dislodge the lead or heart wire with potentially hazardous results. Large control components—usually rotary switches and keyboards—are employed to make it easy for medical personnel to set pacing variables, but these also invite tampering by patient or visitors to the patient's room. Further, such components prevent adequate sterilization of the pacemaker before its use by a different patient. Added is the custom of using short-lived batteries, requiring routine instrument maintenance that sometimes is forgotten under stress, especially since personnel expected to perform such maintenance are unfamiliar with such procedures.

The second primary requirement is that a temporary pacemaker must be easily and readily adjustable. This must be done immediately after connection to the patient, and on some occasions, must be done on an emergency basis during the first crucial hours of a patient's experience with the pacemaker. Because of this requirement, the necessary controls are made relatively large and easy to manipulate. Usually, programming is accomplished by means of push buttons and rotary switches placed on one face of the enclosure. The same face of the box or enclosure must also support one or more readout displays as well. As a result of these combined factors, the temporary pacemaker is much larger than an implantable pacemaker.

These two requirements—proximity to the patient and ready programmability—lead to a series of design conflicts that have not been resolved in the prior art to date. The present invention, however, resolves all of them. The nature of these design conflicts can be appreciated from the following descriptions:

First, one would prefer to attach the temporary pacemaker (hereinafter frequently designated as a unit) to the patient's body, to avoid inadvertent tension on the lead or heart wire. Ideally, it would be attached to the patient's upper arm, chest, or leg using a snug but comfortable strap. Prior art units are much too large to make such a practice convenient or comfortable, however. As a result, the comparatively bulky unit is sometimes tied to the patient's bed, hung on an IV pole, or placed on a nearby table, with a connecting cable provided. With such arrangements, the patient is often unable to move in bed without the hazard of dislodging the lead, a fact that adds mental stress to physical discomfort. In other instances, especially for ambulatory patients, the unit is sometimes pinned to the patient's clothing. All of these arrangements require a longer lead than would a body-mounted unit, though, and both lead length and the relative immobility of the unit increase the possibility of accidentally stressing the lead or heart wire.

The second kind of conflict arises because having a readily adjustable unit situated very near the patient opens the possibility of tampering with the control settings by the patient or visitors. Experience shows that this is a genuine concern, even though it may seem at first to be an implausible one. Remedial changes, both in design and of an ad hoc kind, have proven unsatisfactory. A cover or interlock on the controls has been provided in some cases. But this places an extra burden on medical personnel, who must quickly release the lock, sometimes under stressful conditions. The same is true of interlock arrangements that must be negotiated before settings can be changed. When an unlocked cover is provided, medical personnel have been known to put tape over the cover to make it harder for the patient or visitors to change settings. But this is obviously an unsatisfactory solution, since time-consuming tape removal is a handicap, especially in emergencies, and also the presence of the tape interferes with vision in routine monitoring of the unit.

The third conflict arises because the unit is close to the patient and blood contact is inevitable in the use of the overall system. Therefore, a means of disinfecting the unit is called for by standards of sound medical practice before the same unit is used for a different patient, in spite of the fact that the lead used with the unit is disposable. Such standard practice in this case is augmented by widespread public anxiety concerning HIV infection and AIDS, where human blood is concerned. The units are much too expensive for casual disposal because they are relatively complex and are manufactured in small volumes. But these units are not sealed, so that disinfecting liquids cannot easily and effectively be used. The components cannot withstand temperatures even approaching autoclave temperatures. Furthermore, gas sterilization, although used, is unsatisfactory because literally days are required for aeration, or permitting the toxic sterilizing gases to diffuse out of the many interstices inside the case.

A fourth shortcoming common to all prior art temporary pacemakers is unrelated to the conflicting requirements just cited. It is customary to employ comparatively short-lived batteries to power the unit, with the expectation that the batteries will be checked and usually changed for each new patient. But on occasion this routine step has been neglected with serious consequences. Longer-lived batteries are available, but are most compatible with smaller and more efficient systems.

Another shortcoming and common problem with most patient connected and/or worn medical devices, such as a temporary external pacemaker, is the inadvertent disconnection of the patient lead, thus exposing a serious safety hazard. Currently most patient connections on temporary external patient leads/heartwires are composed of multiple 0.080" diameter straight pins or small diameter wires which are inserted into a female receptacle on the device or an extension cable/adapter that is connected to the device in the same manner. These multiple connections require numerous steps to complete and create multiple chances of disconnection or misconnection. Typically the female receptacle has a locking feature, but what often happens, is the patient's movement will result in the lead or heart wire being pulled out.

The present invention resolves all of the conflicts just outlined. The essential innovation places the bulky control mechanisms in a unit that is separate and that never comes in contact with the patient. By means of infrared radiation, the temporary pacemaker communicates with a small, sealed unit worn by the patient. This resolves the tampering issue, the comfort and convenience issue, and the sterilization issue. In addition, the new, wearable unit of the invention is a natural recipient of a long-lived battery. A multi-conductor connector is also included which reduces the possibility of inadvertent patient lead connecting block removal from the pacing device.

SUMMARY OF THE INVENTION

The general purpose of the present invention is to provide a temporary (or external) pacemaker that resolves the conflicts common to all those of the prior art. It is small, comfortable, tamper-proof, easy to use and monitor, long-lived, safe and sterilizable. The unit worn by the patient employs the combined technologies of the waterproof watch and the implantable pacemaker. The temporary pacemaker is free of all external controls. It incorporates a sealed jack (long a standard component) into which the lead is inserted. The disposable lead is specially designed, including a mechanical connector and shortened length lead for the unit of this invention, and is a major accessory. When using a generic lead or heart wire, a specifically designed connector block is used. The temporary pacemaker unit is worn like a wrist watch, but typically on the upper arm, chest, or leg of the patient, with a disposable strap serving as band, the strap having VELCRO or similar fastening.

According to one embodiment of the present invention, there is provided a wearable temporary pacemaker resembling an implantable pacemaker in shape and size, but differs in that it has an LCD display array clearly visible at its outer face. These displays require extremely small amounts of power, so that the life of the primary lithium battery in the pacemaking unit of this invention will approximate that of a battery in an implanted pacemaker, which is about five years. The LCD array sequentially displays variables sensed and/or paced, as well as the last-set values of the pacing variables. The unit can easily be sterilized by disinfecting liquid and/or gas sterilization after the conclusion of one patient's wearing.

The wearable temporary pacemaker is accompanied by a hand-held remote-control programmer. The programmer is of convenient size, about the size of a pack of cigarettes, and can be stored conveniently, but out of the patient's reach. The programmer includes an LCD readout and programming buttons including a STAT button which automatically transmits a set of predetermined values for all functions of the temporary pacemaker unit. The programmer incorporates an LCD display that presents parameters and values, and a keyboard with dedicated keys for setting each pacing variable. Because of intermittent us, e, its battery will last for approximately a 6–9 months. The programming unit communicates with the wearable temporary pacemaker unit by means of electromagnetic radiation, directed at a sensor located behind a window on the latter, and without physical contact of the two units. It is possible to use visible light, RF, or IR radiation, but the last is preferred. Ambient light can cause problems in the first case. The RF option has the shortcoming that it is less directional than the other two, and use of the programmer for one patient could inadvertently affect the setting of another patient's wearable unit.

According to another embodiment of the present invention, there is provided a patient lead connector block having a female pin connector which engages a male pin connector recessed into a receptacle in the temporary pacemaker case.

The lead wire exits the patient lead/adapter connector block at a right angle which is at 90° from the direction of force required to pull the connector block from engagement with the temporary pacemaker case. If the lead is pulled out with great force, the geometry of the mating features would cause jamming due to the fact that a disconnecting force was not directed along the axis of the connector pins, thus preventing ready disengagement. Pulling straight out on the connector block would, of course, provide for quick and proper disengagement. A color coded area on the sides of the patient lead connector block alert the wearer or other personnel that full engagement has not been ensured. An adapter unit is also illustrated showing the combination of a connector block and lead receptor where generic leads can be connected to the temporary pacemaker.

Significant aspects and features of the present invention include a temporary (external) pacemaking unit that has no controls and is sealed like a waterproof watch or implantable pacemaker.

Another significant aspect and feature of the present invention is the temporary pacemaker unit's small size, which permits the patient to wear it comfortably attached to the upper arm, chest or other part of the body, while affording the patient maximum freedom of motion without hazard to unit or lead, and with reduced mental anguish from fear of accidentally dislodging the lead.

Still another significant aspect and feature of the present invention is a disposable band for attachment of the unit to the patient, the band having a VELCRO or other convenient fastener.

Yet another significant aspect and feature of the present invention is a readout display using LCD technology on the exposed face of the temporary pacemaker unit presenting continuously the most recent setting of each pacing variable, as well as real-time pace and sense indications, and a battery-condition indication.

Another significant aspect and feature of the present invention is a disposable lead to be used for one patient only that plugs into a sealed jack in the pacemaker unit. This lead is designed differently than a standard lead, such that it is shorter to make it safer and more comfortable for the patient. It also has a safer mechanical connector to prevent the lead from disconnecting.

Another significant aspect and feature of the present invention is a connector block/adapter to be used when connecting a heart wire or generic lead to the heart. This adapter is designed for a safer mechanical connection to the unit and to allow the use of a generic lead or heart wire.

Another significant aspect and feature of the present invention is a primary lithium battery that powers the temporary unit, giving it a life of the order of five years.

Still another significant aspect and feature of the present invention is a remote-control programming unit that never makes physical contact with the wearable temporary pacemaker unit or patient, that has large and easy-to-use control elements on it, as well as a display presenting prompting messages, and that communicates with the temporary unit by means of IR radiation, or in the alternative, RF radiation.

Other significant aspects and features of the present invention is a remote-control programming unit that incorporates automatic shut-off.

Another significant aspect and feature of the present invention is a connector block for connection with a temporary pacemaker.

A further significant aspect and feature of the present invention is a connector block having a female plug connector.

A still further significant aspect and feature of the present invention is a temporary pacemaker having a male connector pin recessed into its case.

Yet another significant aspect and feature of the present invention is a connector block which resists inadvertent removal from the temporary pacemaker.

A further significant aspect and feature of the present invention is a color coded area on the connector block indicating that the connector block is not fully engaged.

Another significant aspect and feature of the present invention is an adapter having a lead receptor connected to the connector block so that common pacing leads can be attached to the temporary pacemaker.

Having thus described embodiments and features of the present invention, it is a principal object of the invention to provide a temporary pacemaker of relatively long life, and having no need for routine maintenance such as battery changing.

One object of the present invention is to provide a temporary pacemaker that can be immersed in liquid disinfectant for improved sterilization after use by each patient, or gas sterilization, thus preparing it for use with a further patient.

Another object of the present invention is tamper-proof by virtue of having no external controls to be manipulated by unauthorized persons, such as visitors, or the patient himself or herself.

A further object of the present invention is to provide a temporary pacemaker that is continuously ready for programming, without any time delays caused by unlocking, interlock disabling, or removal of improvised barriers to access.

Still another object of the present invention is to provide localized, noise-immune, reliable communication from unit to unit by IR radiation.

A further object of the present invention is a patient lead connector block which does not inadvertently disengage from a temporary pacemaker.

Yet a further object of the present invention is an adapter for connection of common pace leads to a temporary pacemaker.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
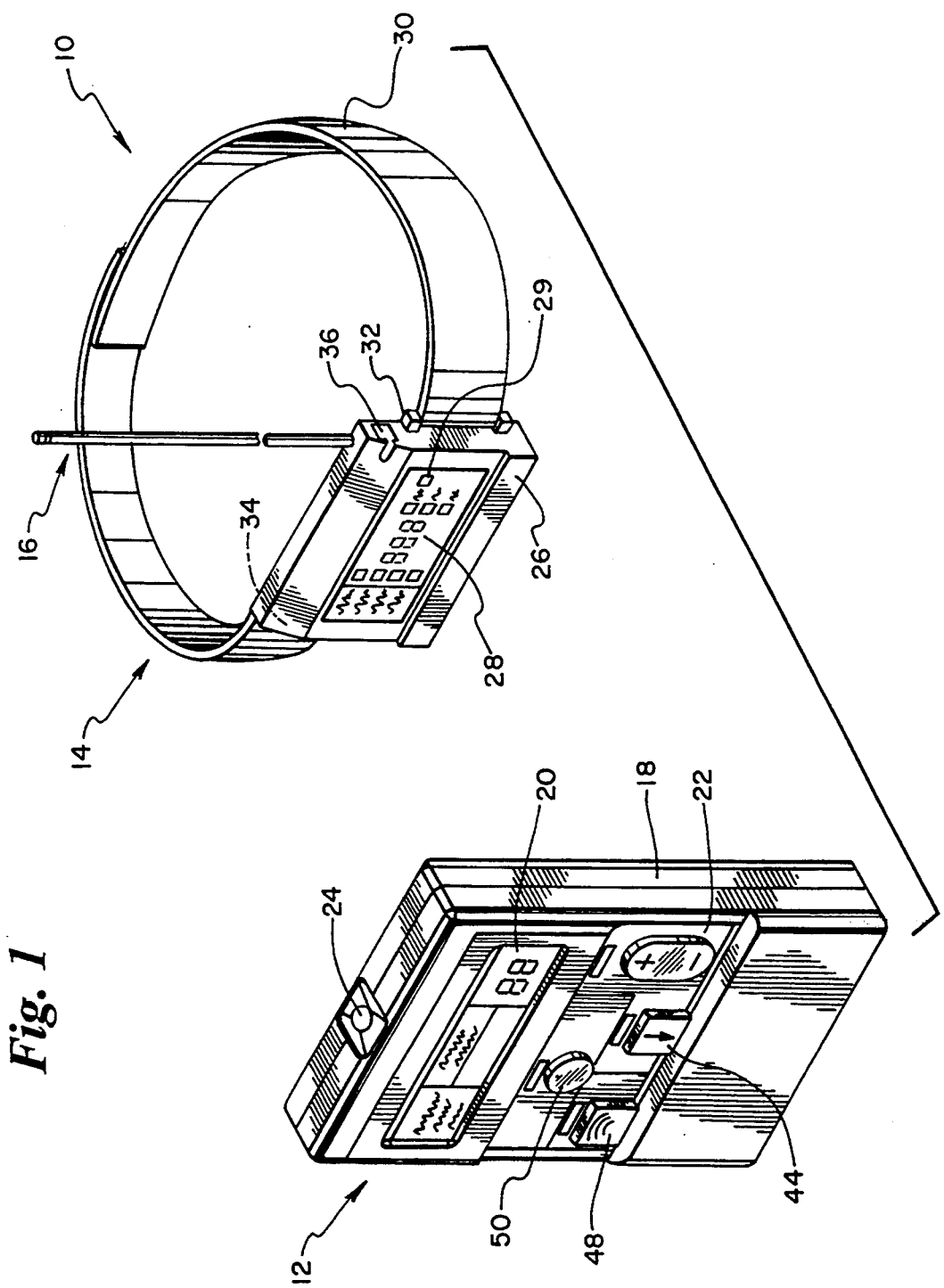
FIG. 1 illustrates a perspective view of the remote control temporary pacemaker system.

FIG. 1 illustrates a perspective view of the remote control temporary pacemaker system 10 including a hand-held remote programmer 12, a temporary pacemaker 14 and a lead 16 secured to the temporary pacemaker 14. The remote programmer 12 includes a case 18, an LCD 20, a control panel 22 and an infrared source 24 through which data is sent to program the temporary pacemaker 14.

The temporary pacemaker 14 includes a water-proof, hermetically sealed case 26, an LCD panel 28, an IR sensing window 29 to communicate with the programmer 12, a disposable strap 30 of suitable length made of foam and VELCRO or other suitable material attached to the case 26 about mounting posts 32 and 34 at opposing ends of the case 26. The lead 16 attaches to the temporary pacemaker 14 by a pacing lead connector block 36. The disposable strap 30 can be of a length suitable for wearing of the temporary pacemaker 14 about the arm of a patient, or in the alternative, can be of a greater length for wearing of the temporary pacemaker 14 about the chest of a patient when the lead 16 is a heart wire exiting the body through the chest wall or even to the leg of the patient.

Figure 2:
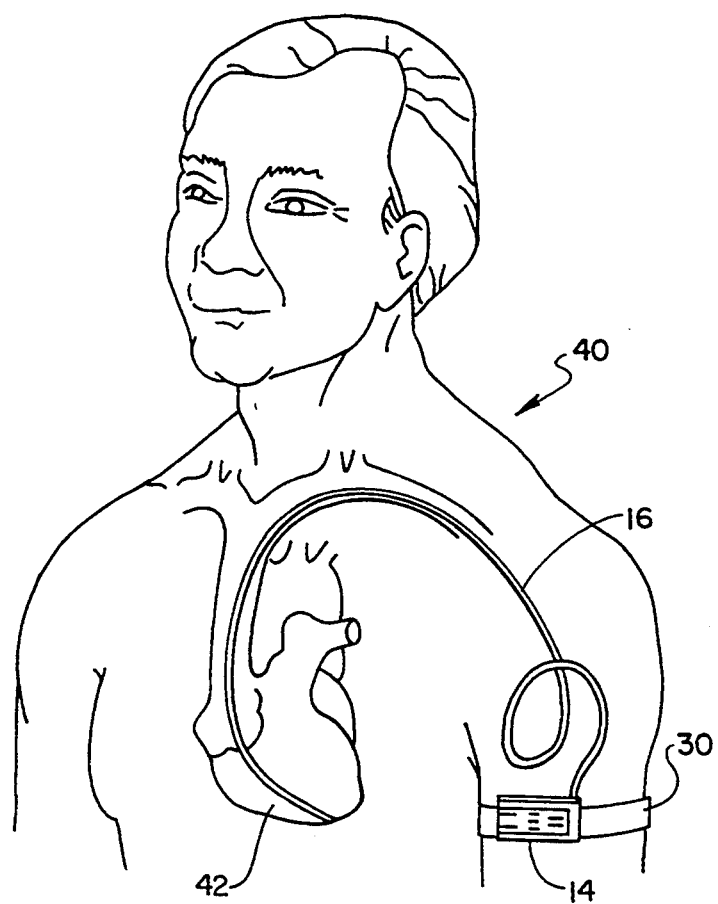
FIG. 2 illustrates a patient wearing the temporary pacemaker.

FIG. 2 illustrates a patient 40 wearing the temporary pacemaker 14 of the present invention attached to the patient's arm by the disposable strap 30, and fitted to a lead 16 that is introduced transcutaneously into the patient's heart 42.

Figure 3:
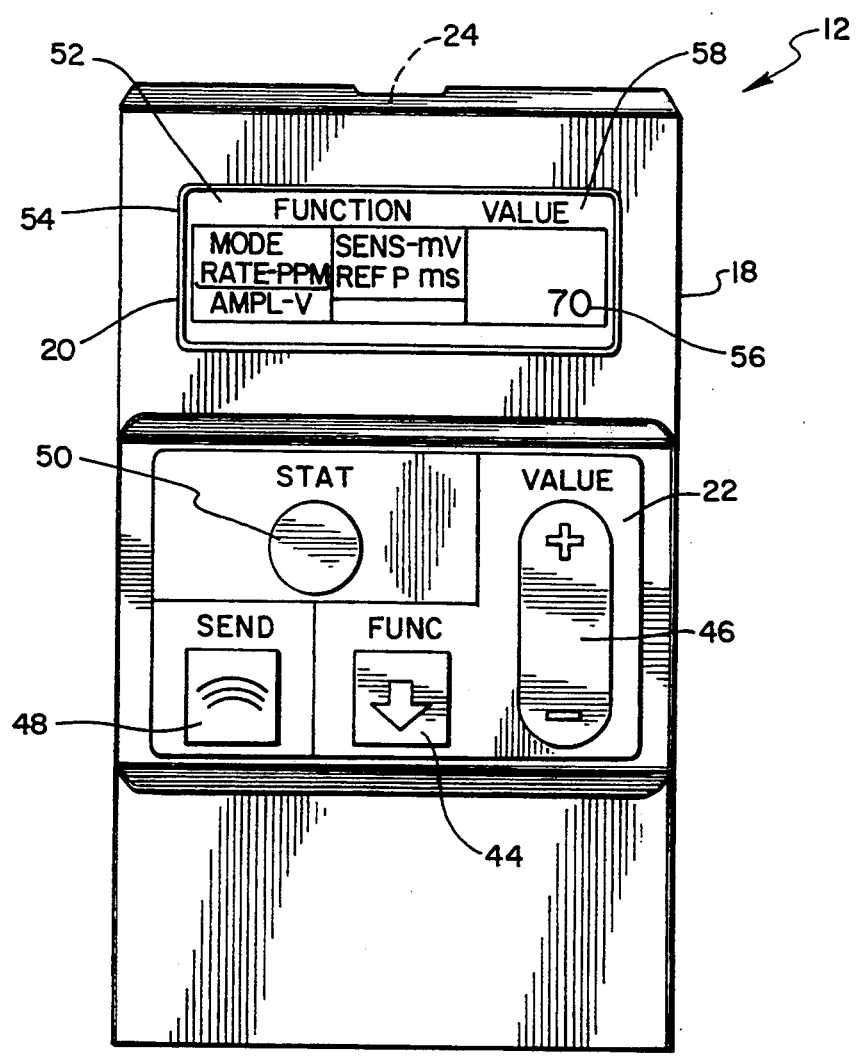
FIG. 3 illustrates a front view of the remote control programmer.
Figure 4:
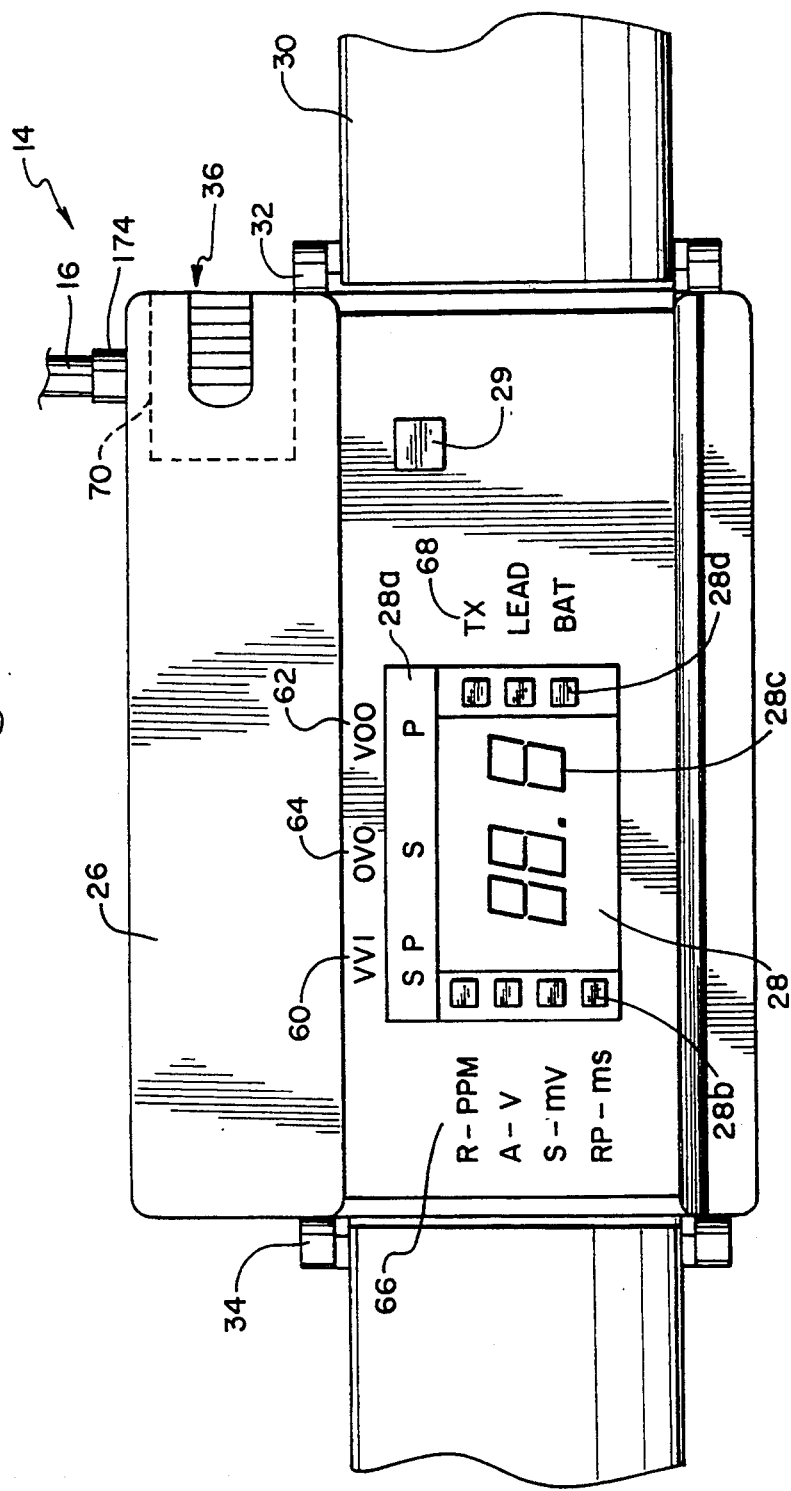
FIG. 4 illustrates a front view of the temporary pacemaker.

FIG. 3 illustrates the remote programmer 12 of the present invention, having keys 44, 46, 48 and 50 in a control panel 22 for setting pacing variables whose values can be read on the temporary pacemaker 14 of FIG. 4, and having an LCD 20 for presenting prompting messages that relate to data to be transmitted to the temporary pacemaker 14 of the present invention. Key 44 is a function key, key 46 is a value key, key 48 is a send (or enter) key and key 50 is a "STAT" key.

Pressing any key 44 through 50 will turn the remote programmer 12 on. If the STAT key 50 is depressed, it will also transmit a group of predetermined STAT settings as well as turn the unit on. The remote programmer 12 will always come on in the nominal settings. These settings are parameter values predetermined by the manufacturer as the norm for external, single chamber pacing. Whereas the STAT settings are emergency settings. The remote programmer 12 will turn off automatically if there have been no key strokes for 120 seconds.

Pressing the "FUNCTION" key 44 scrolls forward through the five programmable functions under the function column 52 starting with "MODE" and ending with "REF P-ms". The function key 44 allows the user to scroll and cycle down through the functions in only one direction. The function chosen will always be highlighted by an underline 54 beneath that function or some other means. Pressing the "VALUE" key 46 scrolls through the values for the function selected by the value key 44. The current value 56 will always be displayed on the right side of the LCD 20 under the value header 58. When the mode function is chosen, all three mode options (VVI, OVO, VOO) will appear under the value header 54 with an underline beneath the mode currently selected. The parameter values will appear one at a time under the value heading 58. Functions/values for the various five programmable functions are as follows:

Modes:
(VVI, OVO, VOO)—Mode options will scroll left to right.
Parameters:
Rate (50–150 PPM incrementing 1 PPM<100 and 5 PPM>100, utilizing two ramping speeds).
Amplitude (0.5–8 volts incrementing 0.5 volts).
Sensitivity (0.5 mV, 1.0, −10 mV incrementing 1 mV, 10–20 mV incrementing 2 mV).
Refractory Period (150–400 ms incrementing 50 ms)

Pressing the "SEND" key 48 transmits the desired function to the temporary pacemaker 14, and A"-S-" will be flashed on the programmed LED 20. Only one function can be sent at a time unless using the "STAT" key. The function being sent must be displayed on the remote programmer 12 at the time it is being transmitted and the programmer should be within 30 inches of the temporary pacemaker 14. The data is transmitted via infrared light pulses generated at the infrared source 24 and received by the temporary pacemaker 14.

Pressing the "STAT" key 50 at any time will automatically transmit a set of predetermined values of all the functions to the temporary pacemaker 14. STAT values are: Mode—VVI, Rate—70 PPM, Amplitude—8 volts, sensitivity—2.0 mV, and refractory period 300 ms.

When the remote programmer 12 battery voltage falls below the minimum specified voltage, the LCD 20 will flash the "L BAT-PROG" message. It will appear at the bottom of the second function column 52. The remote programmer 12 uses one 6 V lithium magnesium dioxide battery.

FIG. 4 illustrates a front view of the temporary pacemaker 14 where all numerals correspond to those elements previously described. The temporary pacemaker 14 can never be turned off completely. It is always programmed at its previous programmed settings and will either be pacing or sensing. If in the VVI mode 60, the temporary pacemaker 14 will sense, and pace only on demand. In the VOO Mode 62, the temporary pacemaker 14 will pace continuously, and in the OVO mode 64, the temporary pacemaker 14 will only sense. The other functions of the temporary pacemaker will always continue to be displayed with the reference to column 66 on the LCD panel 28. The mode of operation VVI 60, VOO 62, or OVO 64 is selected/programmed via the remote programmer 12.

The status of all functions will be displayed at all times. The mode status 60, 62 or 64 will be indicated by a small alphanumeric indicator, "P" for pace and "S" for sense, beneath the selected mode in the LCD subdisplay 28a. Another indicator subdisplay 28b will continuously scroll next to a graphic representation of each parameter shown in column 66 stopping 1½ seconds by each one. As the parameter indicator changes with reference to column 66, a number will appear in the numeric display 28c of the LCD panel 28 which represents the value of the parameter of column 66 being highlighted. LEAD (open lead), BAT (low battery), and TX (transmit error) signals will be displayed via a flashing indicator mark in subdisplay 28d adjacent to column 68 only when they occur.

It is recommended that the user program a patient's temporary pacemaker 14 for the first time prior to connecting it to the patient. This will reassure that the patient receives the correct patient values. The temporary pacemaker 14 only receives one function at a time from the remote programmer 12. The data is transmitted via infrared light pulses from the remote programmer 12 which requires the remote programmer 12 to be within 30 inches of the temporary pacemaker 14. As a check, the temporary pacemaker 14 LCD 28 will display the data upon receiving it. The preprogrammed unit, programmed in the OVO position, is then connected to the patient. At this time, the temporary pacemaker 14 is activated by selecting the appropriate pacing mode WI 60 or VOO 62. After initial programming/set-up has been completed, a function can be reprogrammed at any time without disconnecting the temporary pacemaker 14 or shutting it off.

When the "STAT" key 50 is pressed on the remote programmer 12, the programmer 12 automatically transmits a set of predetermined values mode—VVI, rate—70 PPM, Amplitude—8 volts, sensitivity—2.0 mV, refractory period—300 ms of all the functions to the temporary pacemaker 14. Use of the "SEND" key 48 is not required when transmitting STAT values.

With the use of a disposable patient strap, the device can be positioned on the arm, chest, leg or another part of the body. The pulse generator is designed to be used with a custom or stock lead, or a heart wire. An adapter must be used if using a stock lead or a heart wire.

Figure 6:
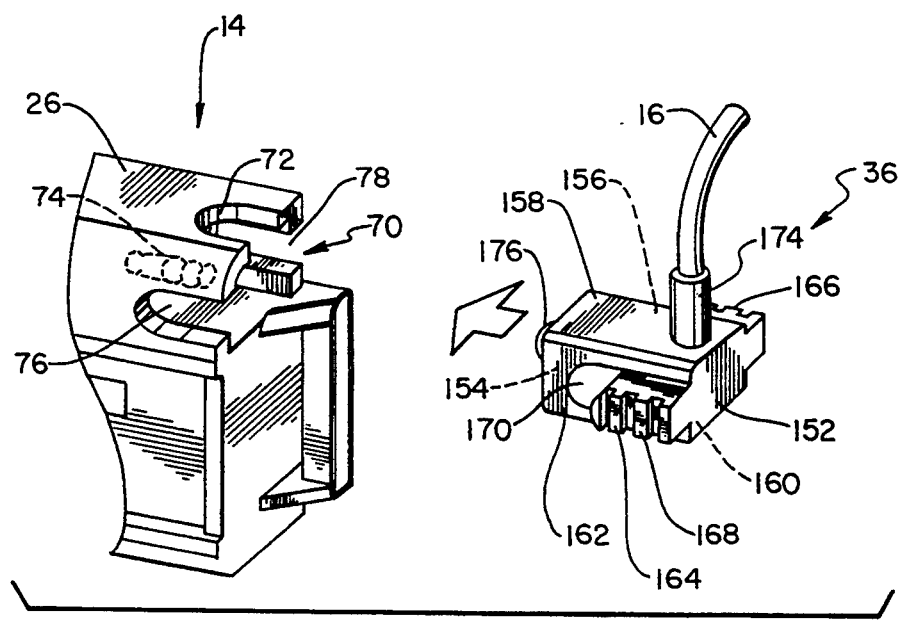
FIG. 6 illustrates a perspective view of a connector block and a temporary pacemaker; and, FIG. 7 illustrates a perspective view of an adapter and a temporary pacemaker.
Figure 7:
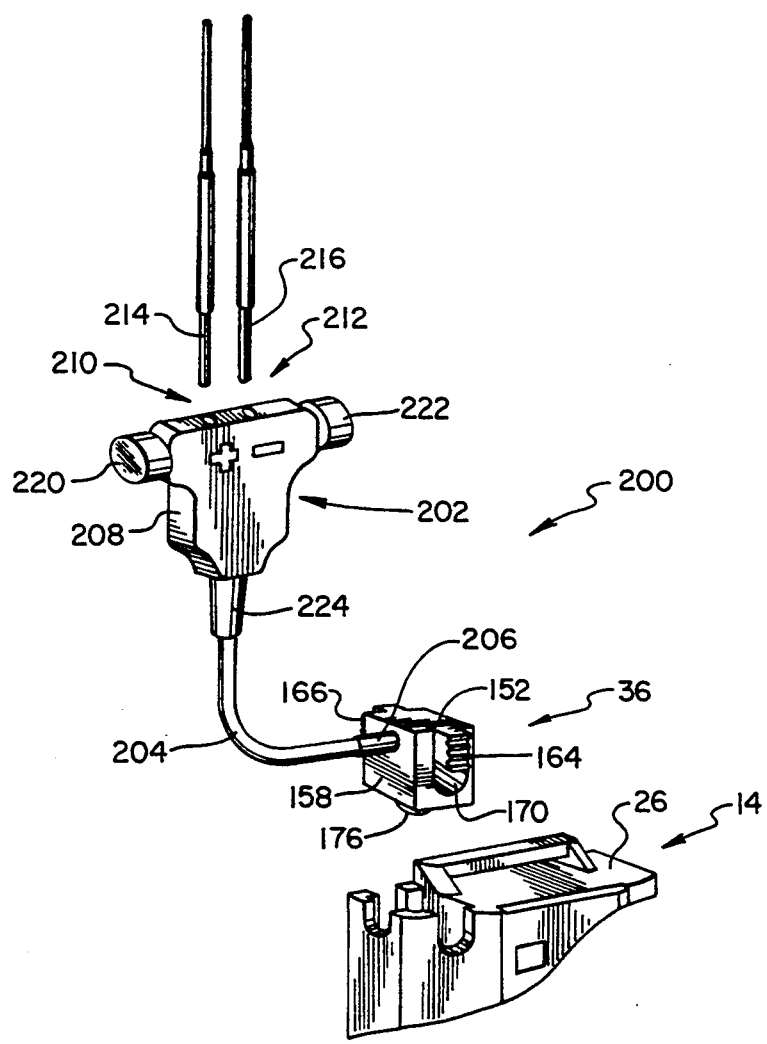

A connector block 36 as illustrated in FIG. 6 aligns in a cavity 70 in the upper right portion of the case 26 to make electrical contact between the temporary pacemaker 14 and the custom lead 16. An adapter connector block 202 illustrated in FIG. 7 is provided should connection to a generic lead or heart wire be required. The temporary pacemaker 14 is also protected from potential damage which could be caused by a defibrillator.

Figure 5:
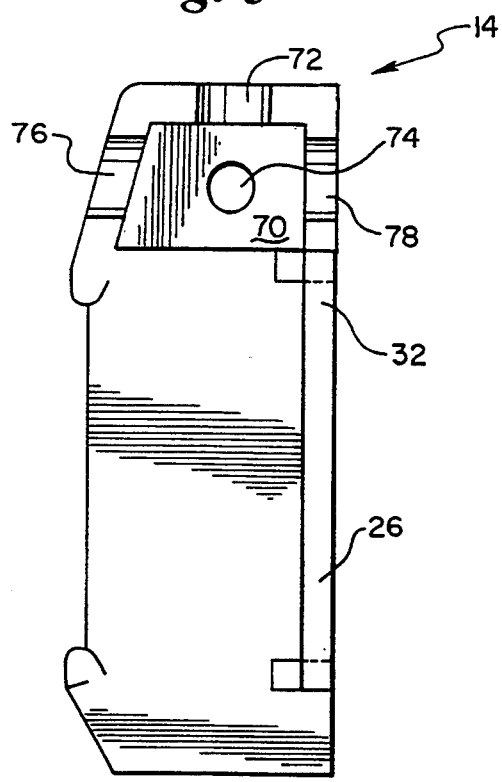
FIG. 5 illustrates an end view of the temporary pacemaker.

FIG. 5 illustrates a right end view of the temporary pacemaker 14 where all numerals correspond to those elements previously described. Illustrated in particular is the connector cavity 70 in the general shape of a quadrilateral having three sides which are either vertical or horizontal and a fourth side which is oblique with references to the other side walls. The unique shape of the cavity 70 allows only for proper orientation of the connector block 36 causing the lead 16 of FIG. 4 to extend vertically through a slotted hole 72 at the top of the cavity 70. A multi-circuit connector pin 74 extends toward the viewer of FIG. 5 for contacting the appropriate internal lead contacts of the connector block 36 of the following FIGS. Alignment slots 76 and 78 on the front and back of the case 26 allow for alignment with corresponding alignment tabs on the connector block 36 as described in the following FIGS. The lead connector offers protection against inadvertent lead pullout from the temporary pacemaker 12, where previous art connectors were often only pins engaged straight way into holes in a simple connector arrangement. The connector block 36 is inserted sideways (to the left) into the cavity 70 and snaps into place. Vertical pull on the lead 16 with subsequent disconnect is very unlikely in that the connector 36 will only disconnect with sideways movement of the right and not with vertical movement. The snap fit of the connector block 36 also discourages removal by inadvertent means.

FIG. 6 illustrates a perspective view of the connector block 36 and temporary pacemaker case 26 where all numerals correspond to those elements previously described. Opposing end surfaces 152 and 154 and adjacent surface 156 are vertical surfaces while surfaces 158 and 160 are opposing horizontal surfaces. Surface 162 is in oblique alignment with the other surfaces 152–160. This geometric configuration allows the connector block 36 to be keyed to the temporary pacemaker case 26 so that there is only one way possible for engagement. Alignment tabs 164 and 166 extend from surfaces 162 and 156, respectively, for alignment with slots 76 and 78 of the case 26. Finger grips 168 are provided on alignment tabs 164 and 166 to provide assistance for insertion and removal. Colored areas or graphic areas 170 are provided adjacent and inboard of alignment tabs 164 and 166 to visually alert a user that the connector block 36 is not completely engaged. A pacemaker lead cable 16, including a strain relief 174 extends vertically and perpendicularly from the top horizontal surface 158 and aligns with the slotted hole 72 in the top of the case 26 when engaged. This results in the lead 16 extending at right angles from the connector block 36 or the direction one would normally pull the connector block 36 out, thus making it more difficult for inadvertent removal of the connector block 36. The lead 16 can be shorter than generic leads, thus making it more comfortable for the patient. An internal female multi-circuit lead pin connector 176 aligns with and connects to the multi-circuit connector pin 74 of the case 26.

Unlike most other temporary external pacemakers that have two or more individual connectors, this device employs a single multi-conductor connector. Thus, connection between the pacing lead, heart wire, etc., and the pacing unit is accomplished by one step instead of many, and the chances of disconnection from the pacing unit are reduced by half or more.

Unlike most other temporary external pacing connections, which employ the female end of the connector on the pacing device, this connector block 36 employs the male end on the pacing device. Thus, the lead or other form of patient connection itself employs the female end of the connector. No other temporary external pacing lead, heart wire, or patient connected cable system employs female receptacles, but employ male connectors on the lead/heart wire end.

This configuration also aids in the cleaning of the pacing unit and reduces the chance of disconnection when combined with the other features of the connector block 36. With the male connector 74 on the pacing unit, there are no holes for blood and/or other contaminants to migrate to.

The connector block 36 consists of a specific design configuration which will key and align the connector position with the temporary pacemaker.

The connector block 36 also employs a graphic feature 170 that will alert medical personnel if the lead or patient connected cable system is inadvertently coming out. When it is fully in place, the graphic indicator on the connector will not be exposed in the slot at the front of the device.

The above disclosed connector can also be designed such that the lead or patient connected cable system comes straight into the connector on the pacing unit, thus, it is in-line or parallel to the direction the male connector is aligned.

FIG. 7 illustrates a perspective view of an adapter 200 incorporating the connector block 36 of FIG. 6 and a lead receptor 202 in combination for use with generic leads or heart wires where all numerals correspond to those elements previously described. A lead cable 204 extends perpendicular from the surface 158 of the connector block 36 and through a strain relief 206 for subsequent connection to generic pacing leads or heart wires. This results in the leads extending at right angles from the connector block 36 in the directions one would normally pull the connector block 36 out, thus making it more difficult for inadvertent removal of the connector block 36. The lead receptor 202 includes a geometrically configured body 208 including female pin connectors 210 and 212 along a top edge for accommodation of generic lead pins or heart wires, such as 214 and 216. The leads need not be a dual set of leads, but may be a unipolar or multiple leads employing one or more separate orifices or grouped together in a multiple connector block. By way of example and for purposes of illustration only and not to be construed as limiting of the present invention, head screws 220 and 222 clamp the generic lead pins 214 and 216 inside the female pin connectors 210 and 212. The lead cable 204 enters the lead receptor 202 through a strain relief 224 and connects appropriately to the female pin connectors 210 and 212.

MODE OF OPERATION

When the temporary pacemaker of the present invention is to be used, a disposable lead that is a special accessory is introduced transcutaneously into the heart of the patient or a heart wire is connected to the heart through the chest wall. The wearable temporary pacemaker unit 14 of the present invention is strapped onto the patient's upper arm, chest or another part of the body, using a disposable strap with a convenient fastening device and the connector end of the lead is plugged into a jack of the waterproof unit.

Using the separate remote-control programming unit of the present invention, a medical person communicates with the wearable temporary pacemaker 14 by means of IR radiation, hand-holding the programming unit 12 close to the temporary pacemaker 14, but not touching it. A compact control panel 22 on the remote programming unit 12 with dedicated buttons is used to set the desired pulse rate, and other relevant variables, with the results of changes being read from the display that is part of the wearable temporary pacemaker 14 and that is in permanent operation. The remote programming unit 12 is then placed in a safe, but convenient storage location that is inaccessible to the patient and visitors to the patient's room.

After use by one patient, the wearable temporary pacemaker 14 is sterilized by means of liquid disinfectants and/or gas sterilization, and is then ready for use by another patient. The remote programming unit 12 has no need for such treatment since it does not touch the patient and poses no risk in any case; it requires only normal protection from its environment, as would any other electronic unit. For the sake of battery life, the remote programming unit 12 shuts itself off after some specified period (such as 120 seconds) after the last key depression.

Connection of a lead to the temporary pacemaker is easily accomplished by inserting the keyed connector block 36 into the temporary pacemaker. The right angle geometry of the connector block minimizes inadvertent lead disconnection. Connection to generic pace leads is also readily accomplished by utilization of the adapter 200 which serves as an interface between the generic lead and the temporary pacemaker.

Various modifications can be made to the present invention with departing from the apparent scope hereof. Communication between the pacemaker and programmer can also be by way of radio frequency signals in lieu of IR signals.

I claim:

1. A lead connector block for connection with a medical device having a connector cavity with a plurality of alignment tabs defined in said connector cavity, comprising:
   a. means for proper orientation of an exterior perimeter of said lead connector block with said connector cavity in said medical device, said means for proper orientation including a specific geometrical shape of said exterior perimeter of said lead connector block, and including at least four adjacent sides and at least one end surface, three of said sides aligned at right angles to each other and a fourth side aligned obliquely to two adjacent of said sides for removable insertion into and alignment with said device in a first horizontal orientation in the direction of said end surface;
   b. opposing alignment tabs extending horizontally from said lead connector block for alignment with said alignment slots in said device;
   c. indication means on said lead connector block for indicating when said lead connector block is not fully inserted or connected with said device;
   d. a female lead pin connector on said end surface; and,
   e. a lead which extends from one of said sides of said lead connector block in a second orientation that is generally perpendicular to the one of said sides and is generally perpendicular to the first orientation.

2. The lead pin connector of claim 1 comprising one or more electrical circuits.

3. The lead connector block of claim 1 comprising means for resisting inadvertent removal from said medical device due to the right angle geometry of the lead extending from said lead connector block.

4. The lead connector block of claim 1 comprising means for engaging said medical device with a snapping action.

5. The medical device of claim 1 comprising a connecting pin which is a male pin.

6. The medical device of claim 1 comprising a connecting pin of one or more electrical circuits.

7. The medical device in claim 1, wherein said lead extends from said lead connector block at a right angle.

8. A lead connector for connection with a medical device having a connector cavity with a plurality of alignment tabs defined in said connector cavity, comprising:
   a. means for proper orientation of an exterior perimeter of said lead connector block with said connector cavity in said medical device, said means for proper orientation including a specific geometrical shape of said exterior perimeter of said lead connector block, and including at least four adjacent sides and at least one end surface, three of said sides aligned at right angles to each other and a fourth side aligned obliquely to two adjacent of said sides for removable insertion into and alignment with said device in a first horizontal orientation in the direction of said end surface;
   b. opposing alignment tabs extending horizontally from said lead connector block for alignment with said alignment slots in said temporary pacemaker device;
   c. a female lead pin connector on said end surface; and
   d. a lead which extends generally perpendicularly from one of said sides of the lead connector block in a second orientation that is also generally perpendicular to the first orientation.

* * * * *